(12) United States Patent
Geisinger et al.

(10) Patent No.: US 10,548,805 B2
(45) Date of Patent: Feb. 4, 2020

(54) VIRTUAL REALITY APPARATUS AND METHODS THEREFOR

(71) Applicant: LIBRA AT HOME LTD, Givat Shmuel (IL)

(72) Inventors: Dario Geisinger, Givat Shmuel (IL); Saul Alberto, Jerusalem (IL)

(73) Assignee: LIBRA AT HOME LTD, Givat Shmuel (IL)

( * ) Notice: Subject to any disclaimer, the term of this patent is extended or adjusted under 35 U.S.C. 154(b) by 0 days.

(21) Appl. No.: 15/398,525

(22) Filed: Jan. 4, 2017

(65) Prior Publication Data
US 2017/0156965 A1  Jun. 8, 2017

Related U.S. Application Data

(63) Continuation-in-part of application No. PCT/IB2015/055071, filed on Jul. 5, 2015.
(Continued)

(51) Int. Cl.
*A61B 3/02* (2006.01)
*A61H 5/00* (2006.01)
(Continued)

(52) U.S. Cl.
CPC .............. *A61H 5/00* (2013.01); *A61B 3/0025* (2013.01); *A61B 3/0041* (2013.01); *A61B 3/113* (2013.01);
(Continued)

(58) Field of Classification Search
CPC .............. A61H 5/00; A61H 2201/0157; A61H 2201/5007; A61H 2201/1604;
(Continued)

(56) References Cited

U.S. PATENT DOCUMENTS 8,494,507 B1  7/2013  Tedesco et al.
8,585,589 B1  11/2013  Cinberg
(Continued)

FOREIGN PATENT DOCUMENTS

WO  2009/129222 A2  10/2009

OTHER PUBLICATIONS

International Search Report for PCT/IB2015/055071, dated Nov. 4, 2015.
Written Opinion for PCT/IB2015/055071, dated Nov. 4, 2015.

*Primary Examiner* — William R Alexander
*Assistant Examiner* — Henry A Duong
(74) *Attorney, Agent, or Firm* — Marc Van Dyke; Momentum IP Group (57) ABSTRACT

A method for treating vestibular impairment, comprising: (a) providing a virtual reality apparatus comprising: a headset; a smartphone having a computer processor, a camera, and a display screen; a case holding the smartphone attaching to the headset; a first optical arrangement, for focusing a field of view of the camera on the user's eye; a second optical arrangement for viewing the display screen; and an application and the processor adapted to display a stimulation exercise on the screen; wherein, the application records movements of the eye, during the exercise, using the camera; wherein the application determines user response competence to the exercise, based upon the movements; and accordingly modifies exercise degree of difficulty; (b) placing the headset on the user's head; (c) focusing the field of view onto the eye; (d) displaying the exercise; and (e) recording eye movements, using the camera.

20 Claims, 7 Drawing Sheets

Related U.S. Application Data (60) Provisional application No. 62/021,028, filed on Jul. 4, 2014, provisional application No. 62/077,332, filed on Nov. 10, 2014.

(51) Int. Cl.
| | |
|---|---|
| *G16H 50/20* | (2018.01) |
| *A61B 3/00* | (2006.01) |
| *A61B 3/113* | (2006.01) |
| *A61B 3/14* | (2006.01) |
| *A61B 5/00* | (2006.01) |
| *A61M 21/02* | (2006.01) |
| *G06F 3/01* | (2006.01) |
| *G06T 11/60* | (2006.01) |
| *A61M 21/00* | (2006.01) |

(52) U.S. Cl.
CPC .............. *A61B 3/14* (2013.01); *A61B 5/6821* (2013.01); *A61B 5/6898* (2013.01); *A61M 21/02* (2013.01); *G06F 3/012* (2013.01); *G06F 3/013* (2013.01); *G06T 11/60* (2013.01); *G16H 50/20* (2018.01); *A61H 2201/0157* (2013.01); *A61H 2201/1604* (2013.01); *A61H 2201/5007* (2013.01); *A61M 2021/005* (2013.01)

(58) Field of Classification Search
CPC ......... A61H 5/005; G06F 3/012; G06F 19/00; G06F 3/013; G06F 19/3481; G06T 11/60; A61M 21/02; A61M 2021/005; G16H 50/20; A61B 5/11; A61B 3/032; A61B 3/00; A61B 3/02; A61B 3/08; A61B 3/0041; A61B 3/113; A61B 3/14; A61B 5/6821; A61B 5/6898; A61B 3/0025; A61B 5/4023; A61B 5/4836; A61B 5/4058; A61B 5/6824; A61B 2562/0219; A61B 5/6829; A61B 5/6828; A61B 5/6803
USPC ........................................................ 351/203
See application file for complete search history.

(56) References Cited

U.S. PATENT DOCUMENTS

| | | |
|---|---|---|
| 2002/0011250 A1 | 1/2002 | Stewart et al. |
| 2004/0006287 A1 | 1/2004 | Epley |
| 2006/0206175 A1 | 9/2006 | Fernandez Tournier et al. |
| 2007/0200927 A1 | 8/2007 | Krenik |
| 2009/0058660 A1 | 3/2009 | Torch |
| 2009/0240172 A1 | 9/2009 | Fernandez Tournier et al. |
| 2010/0079356 A1* | 4/2010 | Hoellwarth .......... G02B 27/017 345/8 |
| 2012/0231931 A1 | 9/2012 | Luberski et al. |
| 2013/0308099 A1* | 11/2013 | Stack .................... A61B 3/113 351/209 |
| 2015/0206329 A1* | 7/2015 | Devries .................. G06T 11/00 345/633 |

* cited by examiner

VIRTUAL REALITY APPARATUS AND METHODS THEREFOR

This application is a continuation-in-part of PCT Application No. PCT/IB2015/055071, which draws priority from U.S. Provisional Patent Applications having Ser. No. 62/021,028, filed Jul. 4, 2014, and Ser. No. 62/077,332, filed Nov. 10, 2014, all of which PCT and Provisional applications are hereby incorporated by reference for all purposes as if fully set forth herein.

FIELD AND BACKGROUND OF THE INVENTION

The present invention relates to viewing apparatus such as virtual reality apparatus, and various methods therefor.

Modern electronic devices as well as worldwide connectivity via the Internet have revolutionized many facets of daily life. Communications, commerce, information movement and management have all be dramatically modified with devices such as smartphones and wireless Internet connectivity. One area that will be greatly affected by the convergence of advanced handheld electronic device and Internet connectivity is in the realm of medicine.

Much of modern medicine is practiced in dedicated medical facilities such as hospitals and clinics. The requirement for both medical experts such as doctors and nurses as well as equipment that can often run into the millions of dollars generally leaves medical treatment at dedicated medical facilities. The challenges of the current arrangement are many: the requirement for travel to a hospital or the like; the general requirement to wait a long time for an appointment as there are too many patients relative to the number of medical professionals; an inability to continue a treatment seriously at home due to the lack of the expensive, sophisticated equipment; and, expense—hospital and similar treatments cost a great deal, whether the patient and/or his/her insurance picks of the tab for various treatments. Bills reaching tens of thousands of dollars for simple surgeries are not uncommon.

While all medical treatments are not necessarily amenable to off-site performance, the proper use of advanced electronic devices such as tablets and smartphones, combined with Internet communication with medical professionals offers the possibility of patients performing many activities away from a formal hospital or clinical setting. Off-the-shelf devices combined with dedicated software and, where required, hardware will allow for many patients to perform exercises at home or at say a nursing home, while a nurse or doctor enjoys real-time access to performance data. The possibility of a medical professional modifying a protocol from afar means that many of the bottlenecks present at hospitals and clinics could be removed.

U.S. patent application Ser. No. 13/477,317 to Luberski and Sumango teaches a system and method for use in moderating symptoms associated with vestibular disorders. The patient stands atop a balance platform and balances or performs other exercises on the platform. The exercises require the patient to work against the instability of an inflatable bladder positioned beneath the balance platform. Training difficult may be increased or decreased by changing the pressure of the inflatable bladder. Increased pressure makes the bladder firm, which is easier to balance upon and decreased pressure softens the bladder, making it more difficult to balance upon. Over time, the repeated performance of the exercise sessions improves the impairment the patient is experiencing due to the symptoms of the vestibular disorder.

U.S. patent application Ser. No. 09/909,084 to Stewart and Wallace describes standardized guidelines for diagnosis and treatment of central nervous system abnormalities such as concussions, head trauma, memory loss, confusion, or other cognitive dysfunction. An initial assessment is made of the person for loss of consciousness, spinal cord injury, or a secondary injury. The person is asked to perform a plurality of mental and physical exercises. A dynamic visual acuity test is also taken. These tests can be performed on the sideline of an athletic playing field to determine whether or not it is advisable for an athlete to return to play. Next, machine-based hearing, dynamic-vision, and balance tests are administered to the patient. The results of these machine-based tests are transmitted electronically to an online database and evaluated by a physician at an off-site location, who prescribes a treatment regimen designed to improve the patient's vestibular functioning.

International Patent Application No. PCT/US2009/040486 to Santina, et al. describes systems and methods for testing vestibular and oculomotor function. One aspect of the invention provides a vestibular and oculomotor function testing device including a track supported by a plurality of bearings, an engine configured to selectively displace the track, and a head coupling component coupled to the track. The head coupling component is configured to convey a movement generated by the engine to a subject's head in one or more axes.

Methods and apparatuses for rehabilitation, particularly for balance and vestibular disorders include BNAVE (Medical Virtual Reality Center University of Pittsburgh) and Balance Quest (Micromedical Technologies), although these systems are unable to perform real-time fusion of visual and vestibular interaction and updating of the displayed image. Equitest (Neurocom, a division of Natus) provides only limited training capabilities. MedFit (Korebalance) provides diagnostic and rehabilitation opportunities and the BRU (Medicaa, Uruguay) provides rehabilitation capabilities, although it is not fit for home use, it is not a portable device and does not incorporate real 3D stimulation nor specific adaptive eye training. Current classic methods for vestibular rehabilitation do not incorporate any technology. In all mentioned cases, there is no way to track home activities and customize the rehabilitation upon home use results.

Balance analysis tools include devices that measure the posture subjected to different sorts of visual, vestibular and proprioceptive stimulation and gait analysis tools by means of accelerometers or cameras that measure different gait parameters while walking on the floor, mattress or treadmill. Examples of posture analysis include Balance Quest (Micromedical Technologies), Balance Manager (Neurocom, a division of Natus) with the Sensory Organization Test (SOT), MedFit (Korebalance), BRU (Medicaa, Uruguay). Gait analysis examples include SensoGo (SensoGo, Israel) and Opal (APDM) that use accelerometer data, while other techniques include cameras recording the body movements, pressure sensing mattresses and gaming hardware such as Kinect (Microsoft). Pressure systems include Walkway (Tekscan) that senses feet pressure.

There is an increase in wellness devices as well that track body movements such as Moov (Mushroom Labs) and Up (Jawbone) which are generally realized as wrist bands.

US Patent Publication Nos. 2006/0206175 and 2009/0240172 disclose methods and apparatus for enabling selective stimulation of oculomotor reflexes involved in retinal image stability.

These advances notwithstanding, the present inventors have recognized a need for improved methods and apparatus for treating brain-related impairments such as vestibular impairments.

SUMMARY OF THE INVENTION

According to teachings of the present invention there is provided a viewing apparatus comprising a headset adapted to be fixed, in a headset donning mode, on, or with respect to, a head of a user; the headset including at least one viewing lens for at least one of the eyes of the user, so as to view a display screen of a mobile computing device, a holding case adapted to fixedly hold the mobile computing device and to reversibly attach to the headset; an optical arrangement associated with the holding case and with the headset, and including at least one optical angle modifier and at least one optical splitter; the headset, the holding case, and the optical arrangement adapted such that, in a viewing configuration of the donning mode, in which the mobile computing device is inserted in the holding case, a display screen of the mobile computing device faces the at least one viewing lens of the headset; wherein the optical arrangement is further adapted to simultaneously establish, in the viewing configuration, a first optical path between the at least one viewing lens of the headset and the camera lens of the mobile computing device; and a second optical path between the display screen of the mobile computing device and the at least one viewing lens of the headset; wherein the at least one optical splitter is optically disposed on the first optical path, between the viewing lens and the at least one optical angle modifier; wherein the at least one optical angle modifier is optically disposed on the first optical path, between the at least one optical splitter and the camera lens; and wherein the at least one optical angle modifier is adapted to modify an angle of incident light received via the at least one optical splitter, and to direct the light towards the camera lens.

According to teachings of the present invention there is provided a monolithic optical adapting arrangement, substantially as described herein.

According to teachings of the present invention there is provided an apparatus for treatment of vestibular, ocular or central impairment, the apparatus comprising: a headset adapted to sit in a donning mode, on a head of a user; a mobile computing device having a computer processor, at least one camera, and a display screen; a case adapted to hold said mobile computing device and to attach to said headset; an optical arrangement associated with said case or said frame, and adapted to focus a field of view of said at least one camera; and an application associated with said processor, said application and said processor adapted to display at least one stimulation exercise on said screen, using virtual reality; said headset, said case, and said optical arrangement adapted such that, in said donning mode: said screen faces eyes of said user, and said optical arrangement focuses a field of view of said at least one camera onto at least one of said eyes; wherein, with said head in said donning mode, said application is further adapted to record movements of at least one of said eyes, using said at least one camera, during said at least one exercise; and wherein said application is further adapted to: perform a determination of a response competence of said user to a particular stimulation exercise of said at least one stimulation exercise, at least partially based upon said movements; and modify a degree of difficulty of said particular stimulation exercise, based upon said determination.

According to another aspect of the present invention there is provided a method for treating a vestibular, ocular, or central impairment of a patient, the method comprising the steps of placing said headset on said head of said user, said case holding said mobile computing device and attached to said headset; focusing said field of view of said at least one camera onto at least one of said eyes, using said optical arrangement; displaying said at least one stimulation exercise on said screen, by means of said virtual reality; recording or measuring said movements of at least one of said eyes, using said at least one camera; performing said determination of said response competence to said particular exercise, at least partially based upon said movements; and modifying said degree of difficulty of said particular exercise, based upon said determination, to produce a difficulty-modified exercise.

According to yet another aspect of the present invention there is provided a method for generating a vestibular or eye rehabilitation protocol comprising: providing at least one stimulus to eyes of a patient; effecting at least one variation of one or more stimulus parameters of said stimulus; tracking at least one of eye, head and body movement of said patient, during said variation, to quantitatively determine a competence of said patient; and creating a stimulation protocol where a determined stimulus parameter is adapted to begin from a value below said competence and to subsequently increase in difficulty.

According to yet another aspect of the present invention there is provided a method for treating a vestibular, ocular, or central impairment of a patient, the method comprising: placing a headset on a head of the patient, said headset including a mobile computing device adapted to include a touch screen, an accelerometer, at least one camera, a computer processor and a digital memory associated therewith, a wireless communication component and an application adapted to run on said mobile computational device, such that said touch screen is disposed in proximity to eyes of the patient, and such that an optical element associated with said headset directs a focus of said at least one camera towards said eyes; providing the patient with a plurality of eye stimuli and head exercises via said touch screen, according to a first protocol, in a particular therapeutic session; recording responses of said eyes and said head to said stimuli using said at least one camera; storing said responses in said memory and analyzing said responses using said computer processor; continuously monitoring said patient performance in response to stimuli by means of head, eye, and body tracking; producing a correlation of expected performance as predicted by said application with an actual performance measured by said processor; and, at least partially based on said correlation, generating a revised protocol for said patient for additional exercises to improve said actual performance.

According to further features in the described preferred embodiments, the determination of said response competence is further based upon a normative response competence.

According to still further features in the described preferred embodiments, the determination of said response competence is further based upon a previous response competence of said user.

According to still further features in the described preferred embodiments, the determination of said response competence is further based upon a target response competence.

According to still further features in the described preferred embodiments, the application is further adapted to perform a determination of a threshold response competence of said user to said particular stimulation exercise.

According to still further features in the described preferred embodiments, the apparatus further comprises at least one accelerometer, at least one of said accelerometer optionally disposed within said mobile computing device.

According to still further features in the described preferred embodiments, the application is further adapted to measure movements of said head, using said at least accelerometer, during at least one head exercise; and the application is further adapted to perform a head-movement based determination of a response competence of said user to a specific head exercise of said at least one head exercise, at least partially based upon said movements of said head; and to modify a degree of difficulty of said specific head exercise, based upon said head-movement based determination.

According to still further features in the described preferred embodiments, the apparatus further comprises at least one of a speaker and a microphone, and the application is further adapted to at least one of: receive user feedback via said microphone and communicate with said user via said speaker during any of said exercises.

According to still further features in the described preferred embodiments, the mobile computing device is selected from the group consisting of a smartphone, tablet computer, digital music player, digital personal assistant, laptop, and mobile computer.

According to still further features in the described preferred embodiments, the mobile computing device is a smartphone.

According to still further features in the described preferred embodiments, the apparatus further comprises a second computing device adapted to receive data from said mobile computing device.

According to still further features in the described preferred embodiments, the mobile computing device is adapted to transfer data and instructions with a remote computing device.

According to still further features in the described preferred embodiments, the apparatus further comprises a database of performance behavior, associated with said computer processor.

According to still further features in the described preferred embodiments, the database includes data pertaining to at least one of: normative performance behavior; performance behavior of users within the same category or having the same profile, and previous performance behavior for said user.

According to still further features in the described preferred embodiments, the is utilized by said processor for at least one of creation, adjustment, customization, and personalization of said at least one stimulation exercise or said at least one head exercise.

According to still further features in the described preferred embodiments, the optical element includes at least one mirror and at least one illumination element arranged to focus said field of view.

According to still further features in the described preferred embodiments, the mobile computing device is adapted to recognize said user according to an eye appearance of said user.

According to still further features in the described preferred embodiments, the headset and said case form a single, integral, monolithic unit.

According to still further features in the described preferred embodiments, the method further comprises applying said difficulty-modified exercise to said user.

According to still further features in the described preferred embodiments, all of the method steps are performed within a single therapeutic session.

According to still further features in the described preferred embodiments, the method is performed in a home setting.

According to still further features in the described preferred embodiments, the method is performed devoid of clinicians.

According to still further features in the described preferred embodiments, the method is performed devoid of clinical supervision.

According to still further features in the described preferred embodiments, the method is applied to Parkinson's Disease, Multiple Sclerosis, risk of fall, migraine related vertigo, concussions or TBI, anxiety disorders, dizziness, phobic postural vertigo and motion sickness.

According to still further features in the described preferred embodiments, the method is applied to a sensory integration deficit involving eyes, head, neck and/or vestibular information.

According to still further features in the described preferred embodiments, the method is applied to children with peripheral disorders, learning disabilities and/or ADHD.

According to still further features in the described preferred embodiments, the method is applied for peripheral vision, vision improvement in health and pathological subjects, reading speed, vision in age-related macular degeneration and/or cognitive control in depression patients.

According to still further features in the described preferred embodiments, the method further includes adding augmented reality data to said screen via a or said second camera associated with said mobile computing device.

Unless otherwise defined here or in the embodiments, all technical and/or scientific terms used herein may have their same meaning as commonly understood by one of ordinary skill in the art to which the term pertains.

"Vestibular", "ocular", and "central" as they relate to brain-related impairments may have their generally understood meaning in the art. "Goggles" may generally refer to an element adapted to be placed on a patient's head and allow for placement of a portion of goggles or associated elements in front of said patient's eyes. A "case" or "goggle case" may generally refer to an element adapted to be attached to a mobile computing device and further allow for attachment of said goggle case to said goggles. A "mobile computing device" may generally refer to a device or element adapted to perform computational actions. Non-limiting examples of a mobile computing device include smartphones, hand-held computers, Google Glass, smart watches, tablet computers, laptop computers, and the like.

An "optical element" or "optical arrangement" may generally refer to an element adapted to allow focus of a patient's eye(s) towards a camera associated with a mobile computing device, like a smartphone. An optical element may generally include mirrors, lights, or other features that allow for monitoring of patient's eye(s) while patient is involved in exercises associated with a protocol according to the instant invention.

"Protocol" may generally refer to a program, application, procedure, or set of instructions adapted to be presented to a patient for performance in the form of exercises. A protocol may be presented automatically or under control of patient or a medical professional. A protocol may be adapted, modified, changed, or altered based on performance of exercises associated with said protocol.

A "headset" may generally refer to a headgear element or arrangement that is adapted to enable the presentation of eye exercises to the eyes of the user, during a donning mode. The headset may allow for tracking of the eyes. Additionally, the headset may allow for tracking of other features of the user, including but not limited to head movements, walking behavior, degree of consciousness, and distraction.

It is understood that an "accelerometer" may be realized as one or more accelerometers, gyroscopes, magnetometers, or the like, as well as combinations thereof.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. Throughout the drawings, like-referenced characters are used to designate like elements.

In the drawings.

DESCRIPTION OF SPECIFIC EMBODIMENTS OF THE INVENTION

The principles and operation of the apparatus and methods of the present invention may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The present invention, in some embodiments, relates to methods and devices for generating and applying a modifiable protocol for a patient with a vestibular or other relevant medical impairment. In some embodiments of the invention, a headset of goggles may be applied to a patient to allow for presentation of stimuli and recordation of performance behavior. The methods herein described can, in some embodiments, be customized for specific patient needs, progress, or developments.

A first aspect of the present invention is a system including a computer or computational device, at least one software application on the device or external thereto (e.g., a cloud-based application), a communication protocol, a virtual reality or augmented reality helmet or goggles or a flat panel display, a head, eye and body tracking device or devices, a stimulus generating system, and a real time visualization tool.

Figures 1A, 1B:
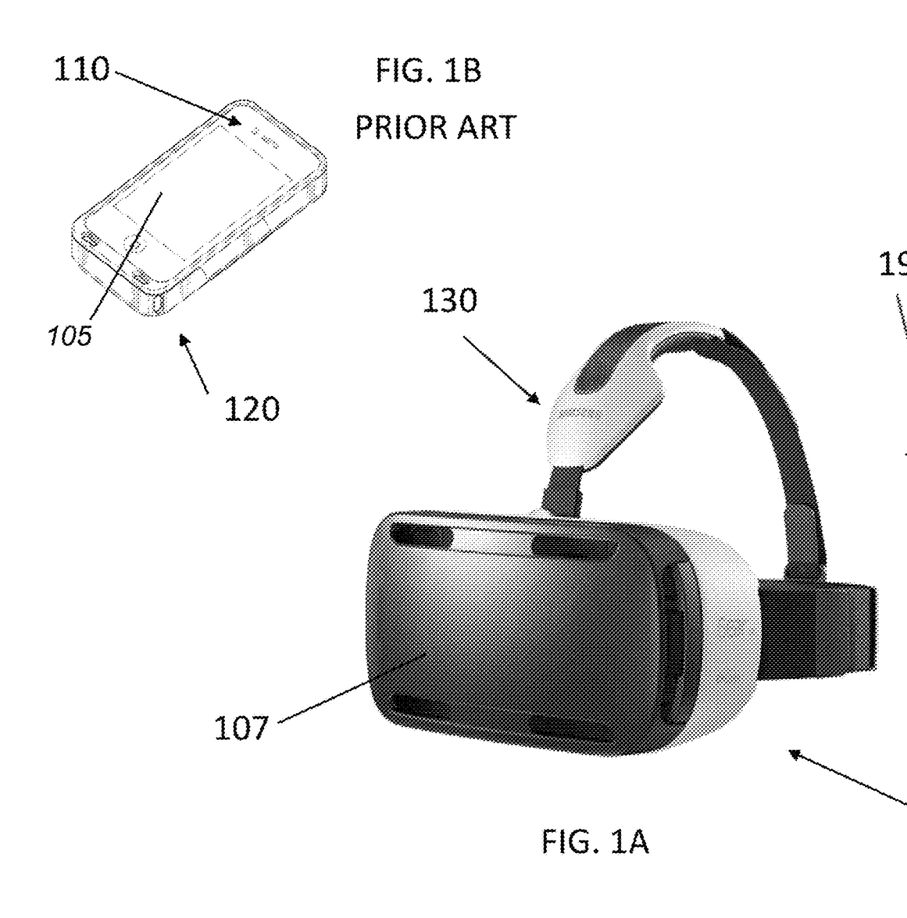
FIG. 1A provides a perspective view of a headset apparatus according to an aspect of the present invention.
FIG. 1B provides a perspective view of a mobile phone having a camera, for use within the apparatus of FIG. 1A.

FIG. 1A provides a perspective view of a headset or headset apparatus 105 according to an aspect of the present invention, the headset adapted to be donned and used by a patient or user having a vestibular impairment (e.g., due to a previous illness).

With reference now to FIGS. 1A and 1B, headset 105 may include a case or goggle case 107 adapted to accept a mobile computing device 120 (typically a mobile phone) having a display screen 115 such as a multi-touch screen, such that when headset 105 is worn by the user in a donning mode, mobile computing device 120 faces the eyes of the user. Case 107 is optionally removable.

It will be appreciated by those of skill in the art that case 107 may be further adapted to accept any one of various mobile computing devices having different geometries. A mobile computing device 120 according to the instant invention may advantageously include a computer processor, at least one camera, and a display screen. More typically, mobile computing device 120 may further include a wireless connectivity function, speaker, microphone, and at least one accelerometer. A camera 110 of mobile computing device 120 is adapted to face the user.

Figure 1C:
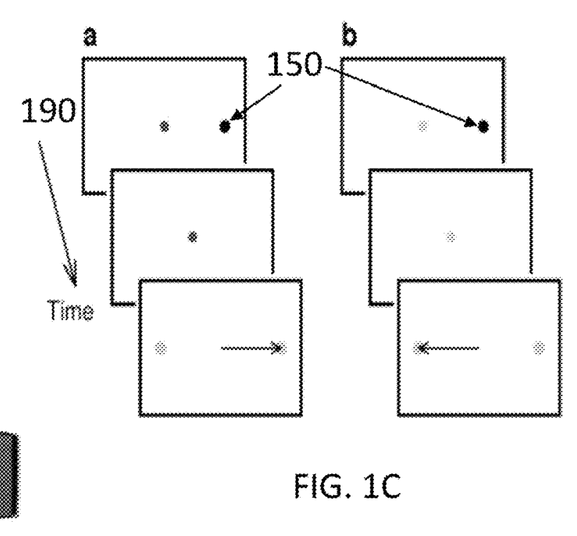
FIG. 1C provides a schematic view of a series of stimuli displayed, over time, to the eyes of the patient by the inventive headset apparatus.

An optical element or arrangement 130 may be adapted to focus the eyes of user on camera 110. In some embodiments this is realized by means of a smartphone or similar mobile communication/computing device. It will be appreciated by those of skill in the art that optical arrangement 130 may include at least one mirror as well as any other elements that allow the eyes to be in focus for camera 110 of mobile computing device 120. The optical arrangement may be attached to headset 105 substantially as shown. Mobile computing device 120 may include a second camera (not shown) facing away from the user, and may be adapted to video the surroundings and to present the surroundings to the user so as to add an element of augmented reality to exercises performed by the user. Referring now to FIG. 1C as well, mobile computing device 120 may be adapted to include and run at least one application for providing stimuli 150 within a successive series of frames a and a series of frames b, series of frames a being displayed to the left eye of the user, successive series of frames b being displayed to the right eye of the user, over time, the progression being denoted by arrow 190. In one example of the stimuli movement, an object is presented to the user. This object moves in the virtual world and is seen by means of the screen. The movement in the virtual world is presented though a set of frames where the object is moving (changing position) in successive frames. When the same image is presented to each eye, the stimulus is seen in two dimensions. When each eye receives a different stimulus, depending on the relative position of the eye to the object, the object is perceived as three-dimensional.

The application may be further adapted to store, analyze, transmit and present results from exercises performed by the user. User eye and head movements may be measured/monitored by at least one accelerometer typically disposed within mobile computing device 120, while speakers associated with the mobile computing device may provide real-time feedback and/or deliver performance information to a non-patient observer or medical care provider.

The system may be adapted to provide visual stimulation that unleashes specific eye movements and head movements that produce dizziness, so as to train the brain to output a suitable vestibular-ocular response. There is also an interaction with the body to combine body-head-eye movements that promotes compensation mechanisms of the brain when some such movements provoke dizziness. The stimulation may replicate already established exercises such as vestibular rehabilitation therapy, (VRT) and aims at unleashing neuroplasticity mechanisms (compensation, substitution and habituation). The same principles may be applied to train eye movements in several different eye pathologies as well.

This system may be extended to incorporate gait analysis while a user is being subjected to visual, vestibular, proprioceptive or/and auditory stimulation.

In some embodiments, the system includes a tablet and a pair of virtual reality goggles having a head tracking system. The user's device is loaded with a training protocol that the user uses as indicated by a suitable clinician (e.g., a physical therapist. By way of example, the protocol may include operating the system twice a day, for 20 minutes each time). Data from the usage is collected and automatically stored in the device. Data may be sent wirelessly to the therapists or by a wired connection on the next appointment. This way the therapists can track and check the correct use of the system. The therapist may utilize a different program that allows for the storing of all information and creating or editing the exercise protocol.

It will be appreciated that various platforms for virtual reality using mobile devices are commercially available, including: Google Cardboard (Google); Pinc (developed by Cordon); VR One (Carl Zeiss); Samsung Gear VR (Samsung Gear); vrAse (vrAse); and DuroVis (DuroVis).

The stimulus generating system may produce at least one of the following types of stimulation:

Saccadic (2D and 3D)—horizontal, vertical, and random, with or without 3D depth, to train quick eye movements; successive saccadic stimulation may be similarly effected, but with successive small saccades defining an eye trajectory, while saccades become less frequent to achieve one large saccade, or by varying the time to achieve the next saccade.

Retinal Optokinetic Stimulation—a flow of objects inside a scene that covers the whole retina.

Foveal Optokinetic Stimulation—a flow of defined objects. The object of interest must be positioned in the fovea, the area of the eye that is able to see details.

Retinal Vestibular-Visual Stimulation—a stimulation that resembles retinal optokinetic stimulation, but also includes head movements that adjust the point of view in the virtual world.

Foveal Vestibular-Visual Stimulation—analogous to retinal vestibular-visual stimulation, in which the object of interest must be positioned in the fovea.

Real Life Locations with Superimposed Stimulation—scenes of commonly used rooms and environments where the stimulation is superimposed.

Head Movement Exercises—while being immersed in a virtual reality scene, the subject is instructed to search for a specific object. To perform the search and explore the scene, head movements are required. When the object is found (e.g., a visual mark is placed over the object), the exercise is over. Information is obtained from an analysis of the movements.

Figure 2:
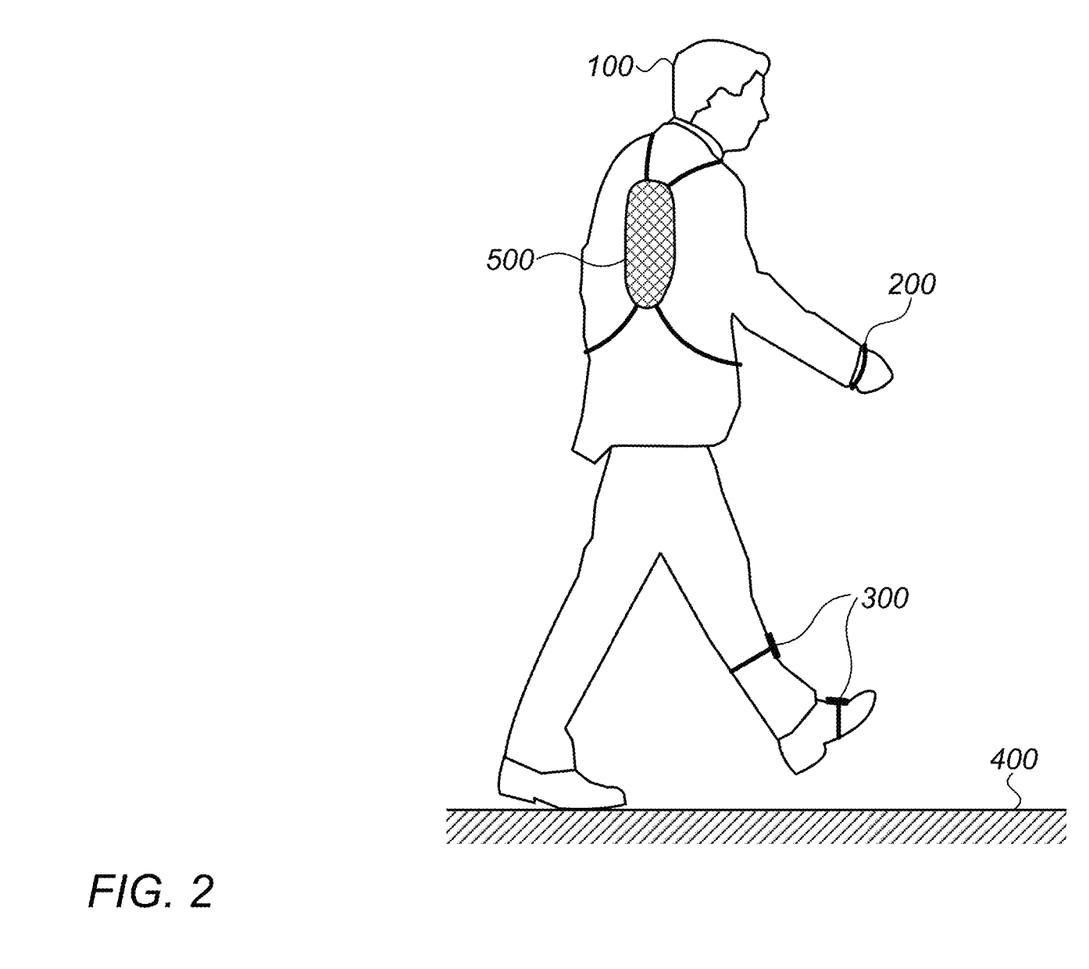
FIG. 2 provides a gait measuring and analysis system that combines body tracking with sensory stimulation, according to an aspect of the present invention.

Referring again to the drawings, FIG. 2 provides a gait measuring and analysis system, according to an aspect of the present invention. The system may challenge the balance system by sensory stimulation. The brain is challenged by different type of sensory stimulation to produce the correct output (e.g., oculomotor and spinal). Different types of stimulation will produce a challenge that, depending on the brain's capacity, will be resolved at certain degree. When the same output is measured under different sensory conditions or sensory stimulation, the capacity of the brain to resolve under those conditions is assessed.

In one exemplary embodiment, a subject dons a pair of virtual reality goggles 100 connected to, or associated with, a stimulus generator device 500 and wearing body tracking accelerometers disposed on the body of the subject, such as leg-mounted accelerometers 300 or wrist-band accelerometers 200. The subject is instructed to walk while the body tracking system records movement and visual stimulation is presented. Real time analysis of the parameters can be used to adjust the stimulation. Further processing determines gait parameters such as cadence, step length, speed, etc, that can be compared to the same set of parameters under different sensory conditions. This may be extended or applied to any type of movement or exercise, any body tracking system and vestibular, proprioceptive and/or auditory stimulation. Visual stimulation may be presented by means of virtual reality goggles (virtual reality or augmented reality); vestibular stimulation by commanding head movements; proprioceptive stimulation by adjusting the surface where the exercises are executed; and auditory stimulation by means of headphones or loudspeakers. The walking surface may be a firm floor or other surface 400 that alters proprioceptive information.

Another embodiment of the invention may include the previous described embodiment where the walking surface is a walking floor mat that has a tilting mechanism adapted to produce an inclination in at least a portion of the mat. The mat is also capable of recording foot pressure. The combination of a Sensory Organization Test (SOT) with gait analysis extends SOT from standing to walking. Balance impairment may be determined by providing sensory stimulation according to a moving pattern of the walking surface. In one exemplary embodiment of the invention, a subject is instructed to walk along a floor mat that senses foot pressure under different sensory conditions. These may include:

eyes closed, firm surface;
eyes open, firm surface;
wearing virtual reality goggles that present stimulation according to the pressure distribution under the feet;
eyes closed, moving surface;
eyes open, moving surface;
wearing virtual reality goggles presenting varying stimulation depending upon the pressure distribution under the feet. The standing surface measures different oscillations of the body sway. The distribution of the body weight under the feet varies due to these oscillations. This distribution can be measured and used to alter the visual stimulation.

SOT is a form of posturography that assess the ability to use visual, proprioceptive and vestibular cues. In the present embodiment, instead of measuring the center of pressure during quiet stance and setting the visual or surface inclination, the information is now used to move the surface on which the subject is walking. The pressure profile during walk is used to determine a virtual center of pressure that is used to modify the display on the virtual reality goggles or/and the inclination of the floor mat.

Information from all tests described above, combined with a permanent body tracking system (such as body tracking accelerometers 200 or 300) can be used to analyze the evolution during the rehabilitation process. During a rehabilitation process, quiet stance, gait parameters and questionnaires are expected to show the evolution of the subject performing the rehabilitation. However, continuous monitoring of the subject generates a significant amount of data that can be correlated with specific patterns of the recorded data. This method can be used to provide metrics to the evolution of the rehabilitation therapy and in long term use, may provide information to correlate the data patterns with specific events (falls, dizziness, etc.) when compared to the subject's own historical data or data collected with respect other subjects.

Monitoring Activities of Daily Living and Assessment of Body Movements

An important element of the rehabilitation is to determine the activities of daily living, since these are an indicator of functional status. Such activities can be tracked by means of sensors worn on the body. FIG. 2 shows an example of such sensors disposed on a wristband or disposed on the legs. Traditional methods for functional assessment of the balance system are based on periodic clinical evaluations. These evaluations test the different systems involved in balance such as eye movements and postural control. Examples include VNG and posturography. These evaluations are discrete assessments that give a picture of patient performance in a clinic environment.

In one embodiment of the present invention, the assessment is extended to a continuous evaluation during the time in which the patient exercises. This assessment is aiming at adapting the stimulation based on patient performance, in real time.

Ultimately, the improvement in quality of life (identified in this case as an increase in daily activities as measured by the sensors) is the objective of the rehabilitation process. The information derived from monitoring patients during the days or weeks in which they perform rehabilitation exercises, is fed into the Initialization of the Parameters of the rehabilitation stimulation as an additional input. The information about daily activities is also available to the therapist to determine the impact of the treatment on daily activities, and complements the traditional measurements that tend to more focus on the response of the different systems involved (e.g., oculomotor response).

Assessment of Body Movements

As an extension to the classic posturography, the inventors have discovered that several other body activities can be performed while being subject to different visual, auditory or proprioceptive stimulation. A patient can be instructed to walk in a straight line while different stimulation is presented. This allows to measure the patient's response to different sensory stimulations under the same body activity. It also allows to compare the results under one type of stimulation and one body activity to patient cohorts. This can be seen as an extension to posturography (standing on a platform under different sensory conditions) and as extension to gait analysis (walking along a mattress with sensors, without changing the sensory conditions). The inventors have discovered that a combination of both approaches, namely, tracking body movements (e.g., gate analysis) while providing sensory stimulation (e.g., visual) provides more and richer information and a more complete functional assessment of the balance system than those attained by traditional methods.

Figure 3:
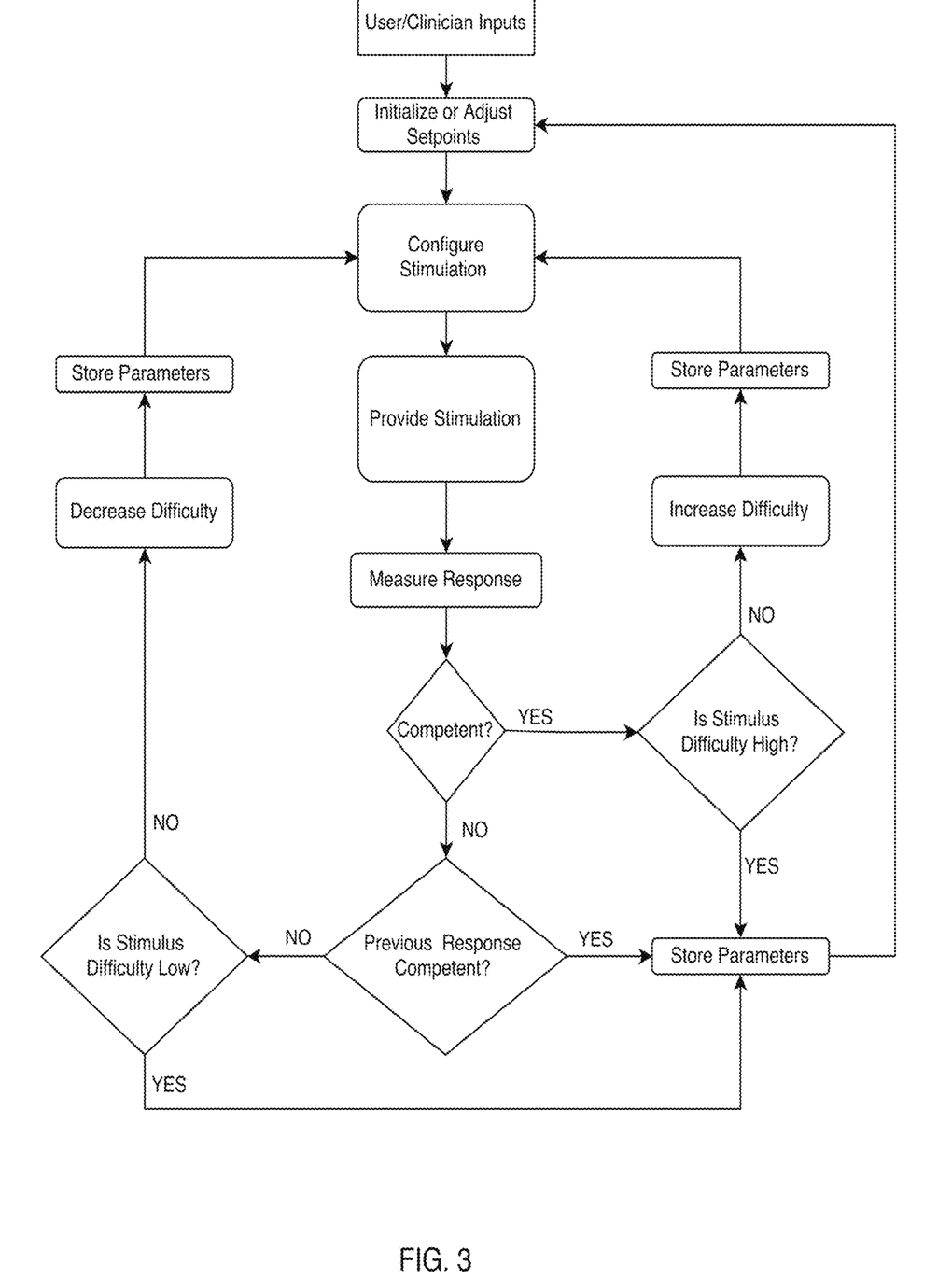
FIG. 3 presents a procedure to determine the threshold of competence for a stimulation, and to generate and deliver successive stimulations.

FIG. 3 presents a procedure to determine the threshold of competence for a stimulation, and to generate and deliver successive stimulations.

The procedure may begin with initialization of setpoints for the particular stimulation procedure being implemented. These setpoints, which may pertain to parameters such as the velocity, size, or frequency of the stimulation, are used to configure the stimulation exercise. The setpoints may also be influenced by user and/or clinician inputs. For example, the system processor may prompt the clinician to rate a particular condition of the patient on a scale of 1 to 5, and subsequently adjust the setpoints accordingly. Similarly, the patient may be prompted to rate various particular patient conditions, e.g., pertaining to mood, alertness, tiredness of the eyes, and headache severity, and based on the input, the system processor may accordingly adjust the setpoints.

The clinician input can also include results from other tests. For example, the clinician may incorporate one of the following:

caloric tests results according to the percentage of asymmetry in the response.
misidentification of the target, tested by increasing velocity of saccades or smooth pursuit while identifying an icon until the icon is misidentified certain percentage of the times.
adjustment of the icon size depending on the automatic dynamic visual acuity test (ADVA).
VNG Results, while using the gain deficit in smooth pursuit, saccades and optokinetic nystagmus to select the exercise and parameters of the stimulation (such as velocity or direction).
sensory organization test (SOT) results. The SOT is a gold standard test that aims at identifying the source of a balance disorder. The outcome of the test will provide information on the contribution of the vestibular, proprioceptive or visual system to the patient's condition. The output of the test can be used to feed our system when producing protocols.

pathology or diagnosis, such as a vestibular or central disorder. The clinician may also specify a non-specific condition such as with respect to elderly population.

Once the stimulation has been configured, the stimulation is administered to the user, for example, a smooth pursuit stimulation, in which the object is a sphere, as shown in FIG. 1C, using the apparatus described with respect to FIGS. 1A and 1B.

The system is adapted to track at least one of the eye movement and the head movement of the user, typically both types of movement, using the on-board camera and accelerometers. Thus, the response of the user to the stimulation is measured or quantitatively determined, instead of relying upon a verbal response from the patient, which couples cognitive issues into the assessment of competence.

Subsequently, the system processor determines the competence of the user response. The determination of user competence includes a comparison between the expected response to the actual response of the user to the stimulation provided. Each type of stimulation may target a different oculomotor response or reflex. In the ideal case, the difference (delta) between the expected response and actual response may tend to zero. In some cases, the expected result is simply the presence of a particular eye movement, while in other cases the existence of the response is complemented with a certain velocity, rate or gain. In the case of a smooth pursuit stimulation, which is a velocity servosystem that allows placing on the fovea an object typically moving at speeds of up to 30 degrees per second, competence is determined if at such speeds, the eyes can gradually follow the object, or whether a corrective quick eye movement is necessary to reach the target. When saccadic stimulation is provided to the patient, competence of the user response is determined by measuring movements that may to some degree overreach or underreach the target. Vestibular ocular reflexes (VOR) are tested by comparing the head and eye movements and determining the degree to which the gain of the movement (head velocity/eye velocity) is close to 1. For various other types of stimulation, the existence of the response may already indicate competence, for example, in optokinetic stimulation, in which the presence of nystagmus is expected.

If the system processor determines the response of the user to be competent, the processor may then increase the difficulty of the stimulation (e.g., by increasing the velocity of the stimulus) for the next session, for the next exercise within the current session, or for the continuation of the current exercise. The parameters may then be stored, and the stimulation is reconfigured.

Optionally, if the system processor determines the response of the user to be competent, the processor may check whether the stimulus difficulty is high (e.g., above a preset value pertaining to a personal or group norm), in which case the stimulus difficulty may be maintained.

If the system processor determines the response of the user to be incompetent, the processor may then decrease the difficulty of the stimulation (e.g., by decreasing the velocity of the stimulus) for the next session, for the next exercise within the current session, or for the continuation of the current exercise. The parameters may then be stored, and the stimulation is reconfigured.

Optionally, if the system processor determines that the previous response of the user was also incompetent, the processor may maintain the stimulation at the current level of difficulty.

Another example where competence is assessed involves a head movements exercise. In this case, a special parameter of interest involves a comparison between the shortest path to the object and the required path. Another special parameter is the velocity of the head movements. In a more general sense, several parameters can be derived from the head movements to compare them to the shortest path to the target. This stimulation can be extended to include eye tracking to compare the actual trajectory of the eyes to the shortest path to find the target. The stimulation described above may include head and eye tracking to compare expected movement to actual movement. This information can be compared with the results of previous exercises (studying the evolution of the response) or to the performance of others (e.g., normative performance). The performance of others may be derived from a normal range or from a range specific for a particular pathology.

In stimulation intended to unleash the ocular movement (e.g., smooth pursuit, saccades, nystagmus and interaction between visual and vestibular systems) using virtual reality, it may be difficult to verify that the stimulation is actually unleashing the expected movement. In order to solve this, some previous approaches have included, in the stimulation, an icon (letters or numbers) that the patient needs to identify, and then enunciate, so that the therapist can verify that the ocular movement is being performed correctly.

The inventors have discovered that stimulation involving the identification of letters or icons targeted at verifying compliance with an exercise, require a second cognitive task that may disadvantageously produce both false positives and false negatives. Subjects may correctly identify the icon, but may have difficulty with the enunciation, due to a variety of factors unrelated to functional competence of the oculomotor system. Subjects may guess the icon based on partial identification. For example: the digits 3, 6, 8 and 9 may be guessed on the basis of similar shapes. False negatives may be attributed to a variety of causes, including lack of attention, cognitive impairment, lack of concentration, visual impairment, decreased acuity and even the effort to produce speech.

The inventors have further discovered that that in order to better assess the functional competence of an oculomotor system (e.g., smooth pursuit), such cognitive tasks may be eliminate or substantially reduced such that the focus may be placed solely on the oculomotor response. By tracking stimuli that target the basics of the oculomotor systems, the online adjustments of the stimulation based on the performance of the subjects may largely eliminate false positives and negatives, thus achieving a more "pure" analysis of the oculomotor system involved.

Figure 4:
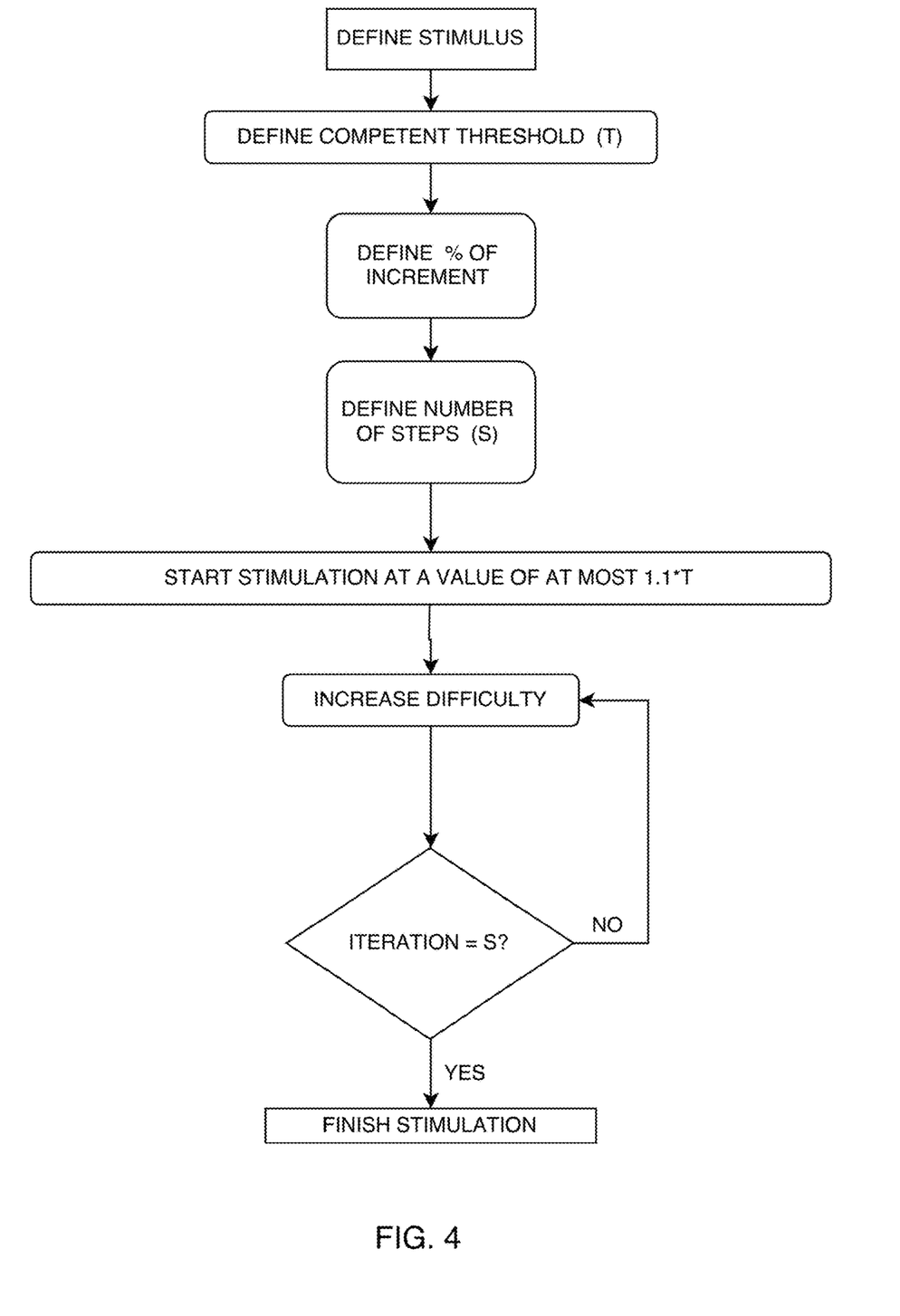
FIG. 4 describes a procedure to generate and deliver successive stimulation in which the level of difficulty is increased around a determined threshold, according to another aspect of the present invention.

FIG. 4 describes a procedure to generate and deliver successive stimulation in which the level of difficulty is increased around a determined threshold, according to another aspect of the present invention. The procedure includes defining a stimulus, providing the stimulus to the patient, measuring the patient response while varying at least one parameter of the stimulus. By way of example, when presenting a stimulus to train smooth pursuit, the velocity of the object is varied until the response is no longer competent. At this point, the threshold of competence is determined. Two more elements may need to be defined: (1) the percentage of increment, which indicates how much the threshold will be surpassed, and (2) the number of steps required to reach the increment. The exercise starts at an initial velocity and is increased based on the elements defined, until the requisite number of iterations is reached.

Specifically, if the intention is to reach 5% above the velocity threshold in 10 steps, the stimulus can be configured to start at 5% below the threshold and increase velocity in each step by 1%. Alternatively, the stimulation can start at the threshold level and increase the velocity 20% above the threshold in two steps. In one example, a smooth pursuit stimulation is determined to be competent at 20 degrees/second, a stimulation is set to start at 21 degrees/second, increasing 5 times in steps of two degrees/second, until reaching 31 degrees/second.

When the number of steps is reached, the process is over.

Another example is to present a saccadic stimulation and subsequently determine user response competence. This competence can represent the maximum velocity that the saccade can have until successive corrective saccades appear to compensate. The stimulation may be provided in several steps, so as to increase the length of the saccade until a certain number of iterations is reached. For example, a saccade competence can be determined to be 100 degrees/second. A stimulus to train this saccadic reflex is set to start at 90 degrees/second and increase in 10 steps of 5 degrees/second (generating longer saccades). In such a case, the first saccade may be at 90 degrees/second, the second saccade may be at 95 degrees/second, until a tenth saccade is presented at 140 degrees/second.

The system may be adapted and configured to track eye movements during stimulus presentation, determine the parameters to be used (e.g., velocity) based on the most challenging parameter in which the brain continues to maintain competency (e.g., in smooth pursuit, when a corrective saccade is required). The system may be adapted and configured to perform a progressive increase of a particular therapeutic parameter from minus delta to plus delta around the point of discontinuity. For example, when a patient is presented with a smooth pursuit stimulation and the velocity of the stimulus is too high, the patient will perform a corrective saccade (i.e., a quick eye movement to continue looking at the point of interest). The velocity where the smooth pursuit is not competent is set as a threshold and the proposed stimulus implies increasing the velocity of the stimulus from a value below competence to a higher value, typically above competence. Another description includes presenting a certain stimulus, determining competence at the exercise and setting the parameters according to the results, for example, setting the velocity of the stimulus based on the threshold determined. Another example is presenting a certain stimulus, determining competence at the exercise and setting the challenging parameter to increase during the same exercise from below competence to above competence. The velocity increments can be configured to increase along a certain period of time (days, weeks), not necessarily during the same session. For example, if the brain is not competent to perform saccades above 10 degrees/second of eye movement, the training could be done using saccades that start at about 6 degrees/second eye movement and increase until 14 degrees/second of eye movement.

The system may send data over a network and receive instructions over a network. The information collected about the usage of the system is uploaded to a central server for remote review. The therapist can update the protocol and send the new version over a network.

The apparatus and methods of the present invention may also be applied to various oculomotor treatments, including poor binocular coordination, convergence insufficiency, amblyopia, diplopia, strabismus, stress-related visual problems, visual rehabilitation, TBI, stroke, whiplash, development delays, and Brock string-like exercises.

In another exemplary embodiment of the invention, a pair of augmented reality goggles may be used to superimpose the stimulation onto the actual environment that the patient or subject is present.

Figure 5A:
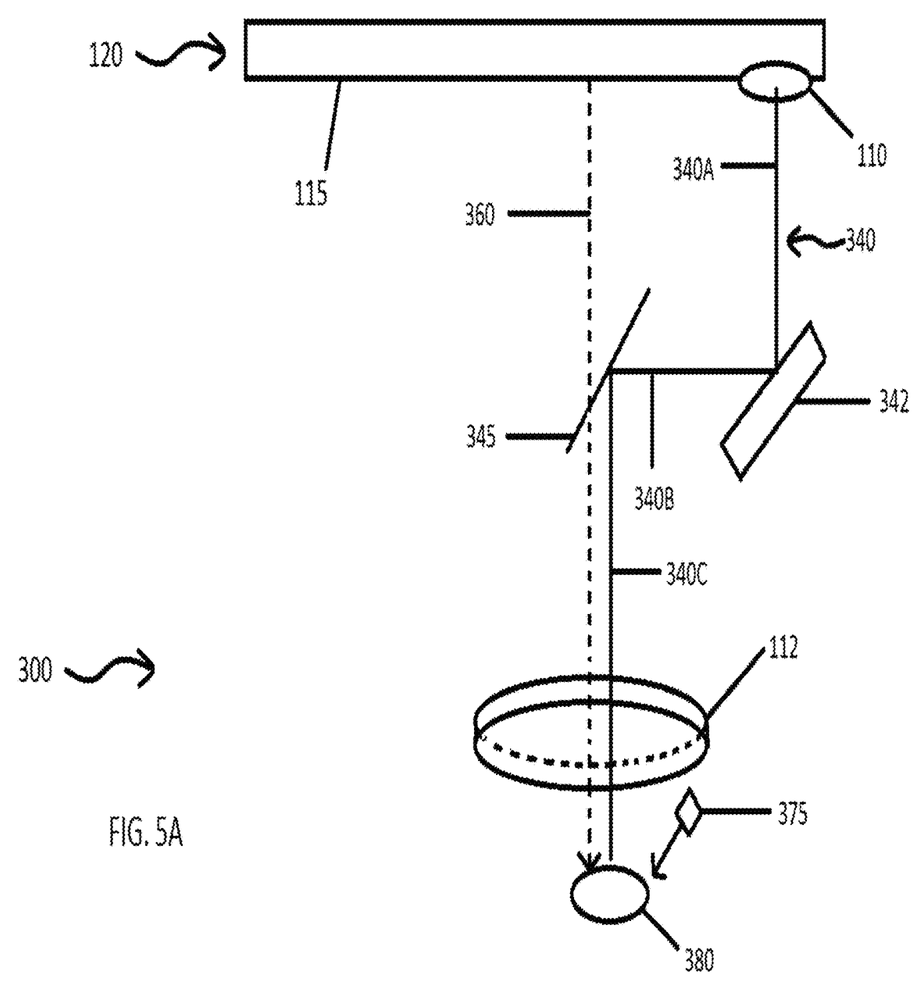
FIG. 5A is a schematic drawing showing the first and second optical paths within the viewing arrangement, according to the present invention.

FIG. 5A is a schematic drawing showing a first optical path 340 and a second optical path 360 within a viewing arrangement or apparatus 300, according to the present invention. The eye 380 of the user views an image displayed by display screen 115 of mobile computing device 120 via second optical path 360. Second optical path 360 includes at least one optical splitter such as beamsplitter 345, and a viewing lens 112.

First optical path 340 may be directed from eye 380 of the user, via viewing lens 112 to at least one optical splitter such as beamsplitter 345. This first section of first optical path 340 is labeled 340C. In a second section 340B of first optical path 340, a portion of the incident light is reflected by the optical splitter towards at least one optical angle modifier 342. In some instances, at least one optical angle modifier 342 may include two or more optical angle modifiers disposed in series.

From the ultimate unit of optical angle modifier 342, the light is directed towards camera lens 110 of mobile computing device 120. This third section of first optical path 340 is labeled 340A.

In some embodiments, a light source 375 may be positioned to direct light at eye 380 of the user. This light source may include visible light and/or infra-red light.

In some embodiments, the optical splitter may include a hot mirror, for use with infra-red light.

Figure 5B:
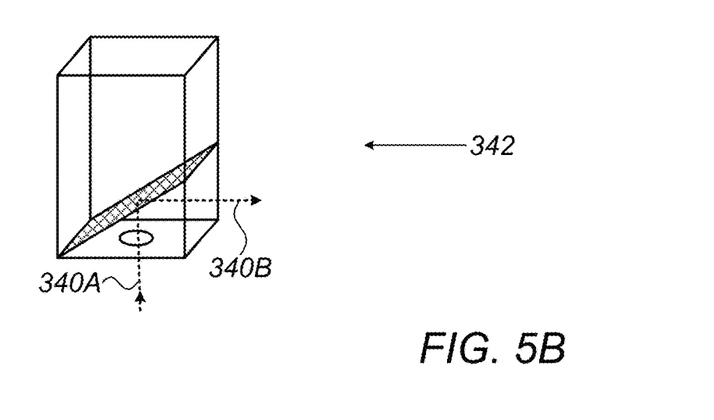
FIG. 5B is a schematic drawing of an exemplary optical angle modifier for use in conjunction with the present invention.

FIG. 5B is a schematic drawing of an exemplary optical angle modifier 342 for use in conjunction with the present invention. Optical angle modifier 342 may typically include a mirror. Other technological alternatives will be readily apparent to those of skill in the art.

Figure 6A:
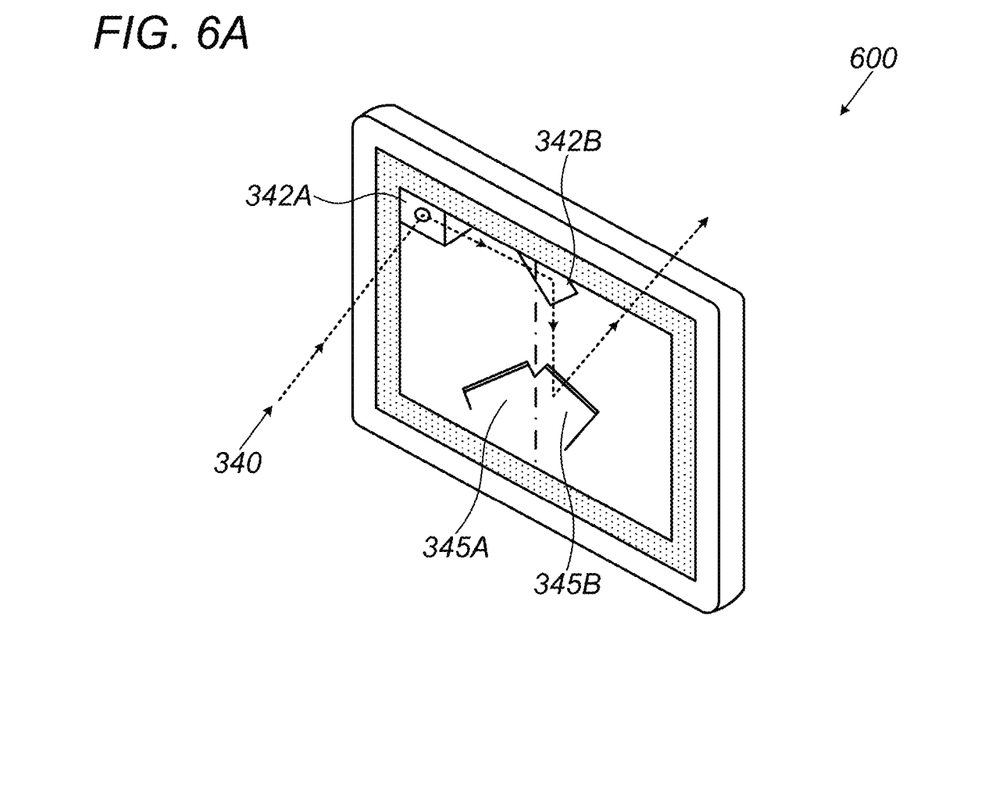
FIG. 6A is a schematic drawing showing an arrangement enabling simultaneous capturing of images of both eyes of the user, according to an embodiment of the present invention.

FIG. 6A is a schematic drawing showing an optical arrangement 600 enabling simultaneous capturing of images of both eyes of the user, according to an embodiment of the present invention. First optical path 340 is directed towards a first optical angle modifier 342A, whose output light is directed towards a second or ultimate optical angle modifier 342B. First and second optical angle modifiers 342A, 342B are adapted and positioned within arrangement 600 such that the output light from the second or ultimate optical angle modifier 342B is directed or largely directed towards a pair of optical splitters such as beamsplitters 345A, 345B. A portion of the incident light is directed by beamsplitter 345A to a first eye (not shown) of the user, and a portion of the incident light is directed by beamsplitter 345B to a second eye (not shown) of the user.

Figure 6B:
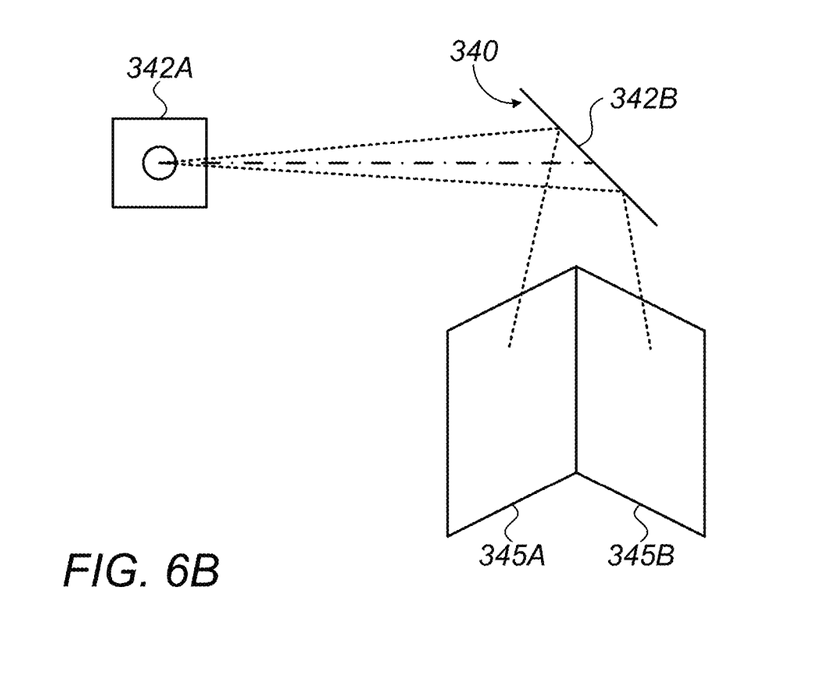
FIG. 6B is a schematic drawing of a portion of the first optical path of the arrangement of FIG. 6A.

FIG. 6B is a schematic drawing of a portion of first optical path 340 of the arrangement 600 of FIG. 6A. It may be observed that the field of view of the camera lens (not shown) sustained via first optical angle modifier 342A broadens as function of distance along the optical path.

Figures 7A, 7B:
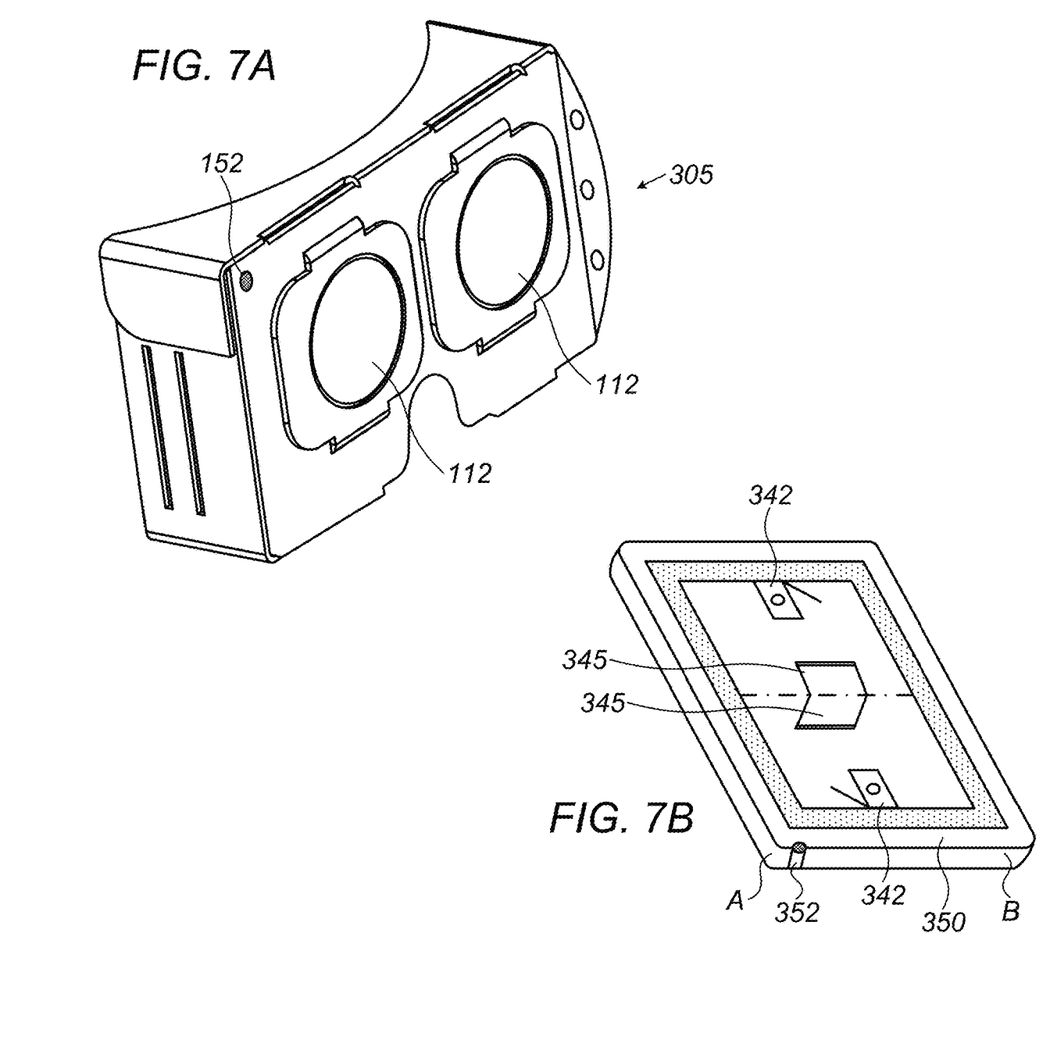
FIG. 7A is a schematic drawing of a headset forming a component of the viewing apparatus according to one aspect of the present invention.
FIG. 7B is a schematic drawing of a monolithic optical adapting arrangement according to one aspect of the present invention.
Figure 7C:
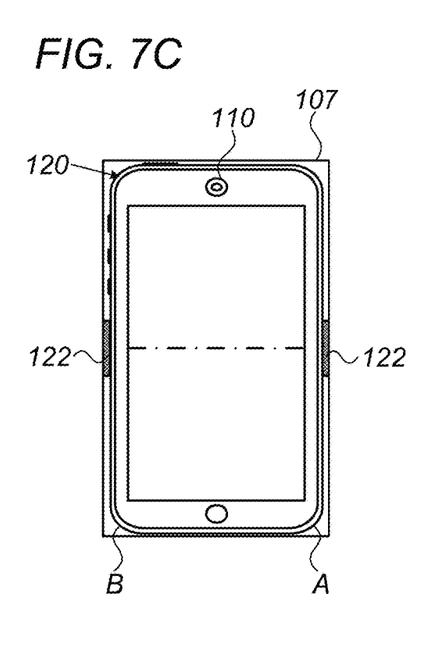
FIG. 7C is a schematic drawing of a holding case forming a component of the viewing apparatus according to one aspect of the present invention.

FIGS. 7A-7C are schematic drawings of components of a viewing apparatus according to aspects of the present invention. FIG. 7A is a schematic drawing of a headset 305 having a pair of headset viewing lenses 112. FIG. 7B is a schematic drawing of an inventive monolithic optical adapting arrangement 350. FIG. 7C is a schematic drawing of a holding case 120 of the viewing apparatus. For the sake of clarity, the figures are provided with identification letters A and B, which represent alignment indicators for the three components (i.e., points A of each component align, as do points B of each component).

As shown, holding case 107 includes a holding mechanism 122 (e.g., spring-loaded) adapted to secure mobile computing device 120 in a fixed position. Holding case 107 may be secured to headset 305 in various ways known to those of skill in the art. Most typically, holding case 107 is secured to headset 305 by sliding the case into a complementary recess in the headset, as may be seen in FIG. 1A.

Monolithic optical adapting arrangement 350 may be secured to headset 305 by a fastener 352. Fastener 352 may form a portion of a fastening arrangement along with a fastener or complementary fastener 152 in headset 305. Such fastening arrangements may include, but are not limited to, hook and loop arrangements, screw and screwhole, clasp arrangements, etc.

According to another aspect of the invention, a method of determining which eye is being tracked may include inserting the phone into the case, identifying the rotation of the mobile phone (computing device) by means of its accelerometers, so as to determine, by means of the mobile phone processor, which eye is being tracked.

EXAMPLES

Reference is now made to the following examples, which together with the above descriptions, illustrate the invention in a non-limiting fashion.

Example 1

A patient who has suffered from a unilateral peripheral vestibular is sent to vestibular rehabilitation and is fitted with a headset adapted to hold a Google Nexus smartphone running an application, wherein the multi-touch screen of the smartphone is adapted to be a few centimeters from the patient's eyes. The headset presents optical elements and lighting conditions that allow one of the phone's cameras to continuously video at least one of patient's eyes. The application presents a set of visual targets via the phone's screen pointing at the patient and also determines eye position for calibration. Afterwards, a physical therapist sets a protocol comprised of a set of exercises that require the patient to perform head and/or eye movements. The application is adapted to present the exercises in the protocol and to record the patient's responses. The patient is instructed to use the system at home 3 times a day (the protocol set by the therapist determines the time which is generally around 15 minutes) The patient fits the Google Nexus into the headset, opens the application and wears the headset with the phone screen facing patient's face. The app detects the eye via a phone camera and any associated optical elements, checks calibration (and updates if necessary) and starts the exercises in the protocol. The application monitors performance and adjusts the complexity of the exercise in case the performance is too poor or too good. All information about usage, adjustments, responses and technical information (low battery, unexpected closing of the app, etc) is recorded by the app and uploaded to a central server. As the patient performs the sessions, the relevant performance information is compared to a cohort database to analyze the evolution of the performance in his/her rehabilitation.

Example 2

A nursing home ward has 3 patients. Patient A, age 78, is prone to falling; patient B, age 82, has age-related macular degeneration; and Patient C, age 68, is a woman having multiple sclerosis (MS). Each patient at his/her appointed time fits the same phone into a provided headset, the appropriate app is turned on, and the headset is fit to be worn by the patient, so that the eyes of the patient are opposite to, and in close proximity with the phone screen. The app is adapted to direct the camera at the eye to identify the user (e.g., pattern recognition of the retina) and will load the protocol set for that specific patient. Recorded information and analysis are stored and uploaded initially on the phone and can be automatically added to an electronic health record.

It will be appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification, including US Patent Publication Nos. 2006/0206175, 2007/0200927, and 2009/0240172, are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method for treating a vestibular, ocular, or central impairment of a user, the method comprising the steps of:
    (a) providing an apparatus comprising:
        a headset adapted to sit, in a donning mode, on a head of the user;
        a mobile computing device integrally including a computer processor having an associated non-transitory digital memory, at least one camera, and a display screen;
        a case adapted to reversibly hold said mobile computing device and to reversibly attach to said headset;
        a first optical arrangement associated with said case, and adapted to focus a field of view of said at least one camera;
        a second optical arrangement associated with said case, said second optical arrangement including a viewing lens; and
        an application associated with said processor, said application and said processor adapted to display at least one stimulation exercise on said screen, using virtual reality;
        said headset, said case, and said first and second optical arrangements adapted such that, in said donning mode:
        said screen faces eyes of said user, and
        said first optical arrangement focuses a field of view of said at least one camera onto at least one of said eyes;
    wherein, with said head in said donning mode, said application is further adapted to record movements of at least one of said eyes, using said at least one camera, during said at least one exercise;

and wherein said application is further adapted to:
perform a determination of a response competence of said user to a particular stimulation exercise of said at least one stimulation exercise, at least partially based upon said movements; and
modify a degree of difficulty of said particular stimulation exercise, based upon said determination;
(b) placing said headset on said head of said user, said case holding said mobile computing device and attached to said headset;
(c) focusing said field of view of said at least one camera onto at least one of said eyes, using said first optical arrangement;
(d) displaying said at least one stimulation exercise on said screen, by means of said virtual reality;
(e) recording or measuring said movements of at least one of said eyes, using said at least one camera;
(f) performing said determination of said response competence to said particular exercise, at least partially based upon said movements;
(g) modifying said degree of difficulty of said particular exercise, based upon said determination, to produce a difficulty-modified exercise; and
(h) applying said difficulty-modified exercise to said user.

2. The method of claim 1, steps (b) to (h) being performed within a single therapeutic session.

3. The method of claim 1, wherein said mobile computing device is a smartphone.

4. The method of claim 1, wherein the user has at least one of Parkinson's Disease, Multiple Sclerosis, risk of fall, migraine related vertigo, concussions or TBI, anxiety disorders, dizziness, phobic postural vertigo and motion sickness.

5. The method of claim 1, wherein the user has a sensory integration deficit involving eyes, head, neck and/or vestibular information.

6. The method of claim 1, wherein the user has at least one of peripheral disorders, learning disabilities and ADHD.

7. The method of claim 1, wherein said method is applied so as to improve at least one of peripheral vision, vision in health and pathological subjects, reading speed, vision in age-related macular degeneration, and cognitive control in the user, the user being a depression patient.

8. The method of claim 1, further including adding augmented reality data to said screen via an external camera or a second camera associated with said mobile computing device.

9. The method of claim 1, wherein said determination of said response competence is further based upon a normative response competence.

10. The method of claim 1, wherein said determination of said response competence is further based upon a previous response competence of said user.

11. The method of claim 1, wherein at least a portion of both of said first and second optical arrangements is built into a monolithic optical adapting arrangement.

12. The method of claim 1, wherein said determination of said response competence further based upon a target response competence.

13. The method of claim 1, said application being further adapted to perform a determination of a threshold response competence of said user to said particular stimulation exercise.

14. A method for treating a vestibular, ocular, or central impairment of a user, the method comprising the steps of:
(a) providing an apparatus comprising:
a headset adapted to sit, in a donning mode, on a head of the user;
a smartphone having a computer processor having an associated non-transitory digital memory, at least one camera, and a display screen;
a case adapted to reversibly hold said smartphone and to reversibly attach to said headset;
a first optical arrangement associated with said case, and adapted to focus a field of view of said at least one camera;
a second optical arrangement associated with said case, said first optical arrangement including at least one optical splitter and said second optical arrangement including a viewing lens; and
an application associated with said processor, said application and said processor adapted to display at least one stimulation exercise on said screen, using virtual reality;
said headset, said case, and said first and second optical arrangements adapted such that, in said donning mode:
said screen faces eyes of said user, and
said first optical arrangement focuses a field of view of said at least one camera onto at least one of said eyes;
wherein, with said head in said donning mode, said application is further adapted to record movements of at least one of said eyes, using said at least one camera, during said at least one exercise;
and wherein said application is further adapted to:
perform a determination of a response competence of said user to a particular stimulation exercise of said at least one stimulation exercise, at least partially based upon said movements; and
modify a degree of difficulty of said particular stimulation exercise, based upon said determination;
(b) placing said headset on said head of said user, said case holding said smartphone and attached to said headset;
(c) focusing said field of view of said at least one camera onto at least one of said eyes, using said first optical arrangement;
(d) displaying said at least one stimulation exercise on said screen, by means of said virtual reality; and
(e) recording or measuring said movements of at least one of said eyes, using said at least one camera.

15. The method of claim 14, further comprising, prior to step (b): securing said smartphone to said case, and subsequently, securing said case to said headset.

16. The method of claim 14, further comprising, prior to step (b): sliding said case into a recess in said headset.

17. The method of claim 14, wherein said first and second optical arrangements form a monolithic optical arrangement reversibly fastened to said headset.

18. The method of claim 17, wherein said monolithic optical arrangement is reversibly fastened to said headset by a complementary fastening arrangement.

19. The method of claim 14, wherein said first optical arrangement is adapted to focus said field of view of said at least one camera via said viewing lens.

20. The method of claim 14, wherein said at least one optical splitter is built into a monolithic optical adapting arrangement.

* * * * *